(12) United States Patent
Pappas et al.

(10) Patent No.: US 7,485,147 B2
(45) Date of Patent: Feb. 3, 2009

(54) ANKLE PROSTHESIS INCLUDING TIBIAL COMPONENT HAVING PERIPHERAL WALL FOR PREVENTING THE FORMATION OF BONE CYSTS

(76) Inventors: Michael J. Pappas, 8650 S. Ocean Blvd., Jensen Beach, FL (US) 34987; Frederick F. Buechel, 61 First St., South Orange, NJ (US) 07079

( * ) Notice: Subject to any disclaimer, the term of this patent is extended or adjusted under 35 U.S.C. 154(b) by 398 days.

(21) Appl. No.: 11/049,813

(22) Filed: Feb. 3, 2005

(65) Prior Publication Data
US 2005/0182492 A1   Aug. 18, 2005

Related U.S. Application Data

(60) Provisional application No. 60/544,911, filed on Feb. 13, 2004.

(51) Int. Cl.
*A61F 2/42* (2006.01)
(52) U.S. Cl. ............... 623/21.18; 623/20.18; 623/18.11; 623/17.15
(58) Field of Classification Search ............... 623/18.11, 623/20.18–20.33, 21.18–19
See application file for complete search history.

(56) References Cited

U.S. PATENT DOCUMENTS

| 4,470,158 | A | * | 9/1984 | Pappas et al. ............ 623/20.21 |
| 5,314,486 | A | * | 5/1994 | Zang et al. ............... 623/21.19 |
| 5,507,821 | A | * | 4/1996 | Sennwald et al. ........ 623/21.13 |
| 6,409,767 | B1 | | 6/2002 | Perice et al. |

FOREIGN PATENT DOCUMENTS

DE   101 23 124 C1   12/2002
FR   2 676 917 A1   12/1992

* cited by examiner

*Primary Examiner*—Corrine McDermott
*Assistant Examiner*—Christohper D Prone
(74) *Attorney, Agent, or Firm*—Gerald E. Hespos; Anthony J. Casella

(57) ABSTRACT

The tibial component of a prosthetic ankle joint including a tibial component, a talar component, and an intermediate sliding plastic bearing, with the tibial component including a depending peripheral wall that surrounds and is spaced from the plastic bearing and is intended to reduce rubbing of the plastic bearing against tissue which would produce wear particles that lead to the formation of bone cysts. The depending peripheral wall of the tibial component is intended to reduce such possible abrasions by at least partially shielding the plastic bearing from the surrounding tissue.

17 Claims, 4 Drawing Sheets

ANKLE PROSTHESIS INCLUDING TIBIAL COMPONENT HAVING PERIPHERAL WALL FOR PREVENTING THE FORMATION OF BONE CYSTS

This application claims the benefit of Provisional Patent Application No. 60/544,911 filed Feb. 13, 2004.

BACKGROUND OF THE INVENTION

1. Field of the Invention

A prosthetic ankle joint is provided with a tibial component, a talar component, and an intermediate sliding plastic bearing. The tibial component includes a depending peripheral wall that surrounds the bearing and is intended to reduce rubbing of the plastic bearing against tissue which could produce wear particles that lead to the formation of bone cysts. The peripheral wall is intended to reduce such possible abrasions by at least partially shielding the bearing.

2. Description of the Related Art

The existing Buechel-Pappas Total Ankle Replacement System, which was invented by the applicants of the subject invention, is a time-tested, total ankle replacement system which is a result of more than 30 years of development, clinical investigation, and use.

The Buechel-Pappas Total Ankle Replacement System is described in detail in U.S. Pat. No. 4,309,778 which is entitled "NEW JERSEY MENISCAL BEARING KNEE REPLACEMENT" which issued on Jan. 12, 1982, the disclosure of which is incorporated herein by reference.

The Buechel-Pappas Total Ankle Replacement System is also described in U.S. Pat. No. 4,340,978 which is entitled "NEW JERSEY MENISCAL BEARING KNEE REPLACEMENT" which issued on Jul. 27, 1982, the disclosure of which is incorporated herein by reference.

Notwithstanding the success of the Buechel-Pappas Total Ankle Replacement System which is the subject of U.S. Pat. Nos. 4,309,778 and 4,340,978, it has been discovered that for several reasons, including components that are too large and growth of tissue into the joint space between the components of the ankle prosthesis, rubbing of the plastic bearing against tissue produces wear particles. In turn, the wear particles lead to the formation of bone cysts.

It is the object of the subject invention to minimize this potential problem by providing a new and improved tibial component as part of the Buechel-Pappas Total Ankle Replacement System.

It is a further object of the subject invention to provide a new and improved tibial component of the Buechel-Pappas Total Ankle Replacement System which allows easy insertion of the intermediate plastic bearing during the surgical procedure of implanting the ankle in a patient.

SUMMARY OF THE INVENTION

The subject invention provides a new and improved tibial component for the Buechel-Pappas Total Ankle Replacement System which includes a depending wall extending around the entire periphery of the base or inferior surface of the tibial component. In an alternate embodiment, the depending wall extends around three sides of the inferior surface of the tibial component, with the anterior inferior wall area being open to facilitate insertion of the plastic bearing between the tibial component and the talar component during the implant surgical procedure.

The depending wall extending from the inferior surface of the tibial component is intended to reduce possible abrasion between the plastic bearing and tissue by effectively shielding the bearing from the tissue.

Clearance is provided between the depending wall of the tibial component and the plastic bearing so that usually there will not be contact between the plastic bearing and the inside surface of the peripheral wall. The curvature of the tibial depending wall and the curvature of the sides of the plastic bearing sides are configured to reduce contact stresses therebetween in the event that touching of those surfaces does occur during flexure of the ankle prosthesis.

In one embodiment of the subject invention, the depending wall extends along the entire periphery of the tibial plate while, in another embodiment, an opening in the wall is present along the anterior portion of the inferior surface of the tibial component to allow easy insertion of the plastic bearing during a surgical procedure for implanting the replacement ankle prosthesis.

DETAILED DESCRIPTION OF THE PREFERRED EMBODIMENTS

Figure 1:
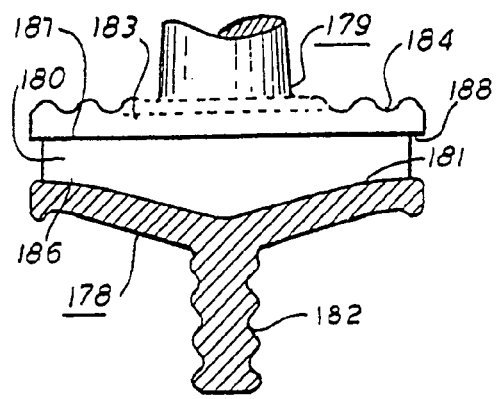
FIG. 1 is a cross-sectional view of the prior art Buechel-Pappas Total Ankle Replacement System taken along lines 1-1 in FIG. 3.
Figure 2:
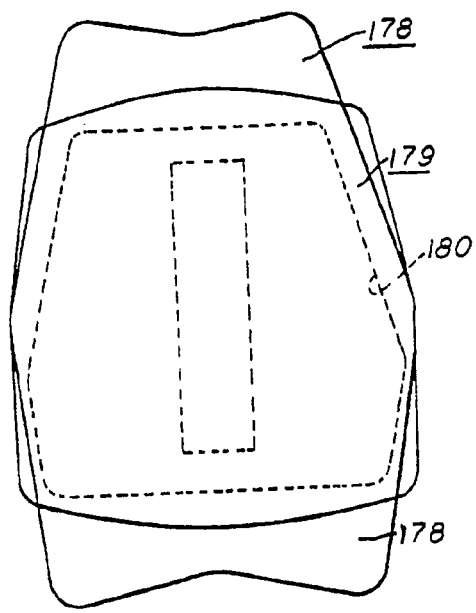
FIG. 2 is a top plan view of the prior art Buechel-Pappas Total Ankle Replacement System.
Figure 3:
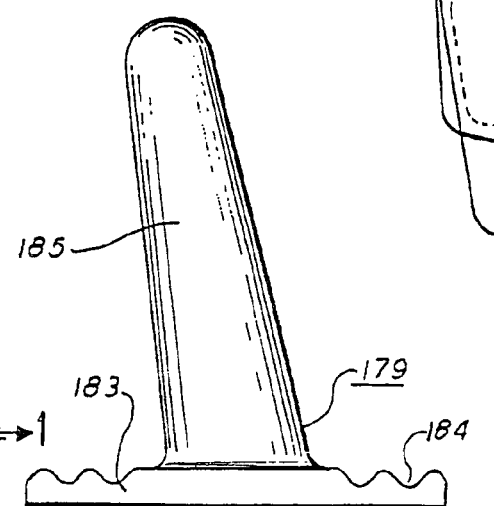
FIG. 3 is a side elevational view of the prior art Buechel-Pappas Total Ankle Replacement System.
Figure 3:
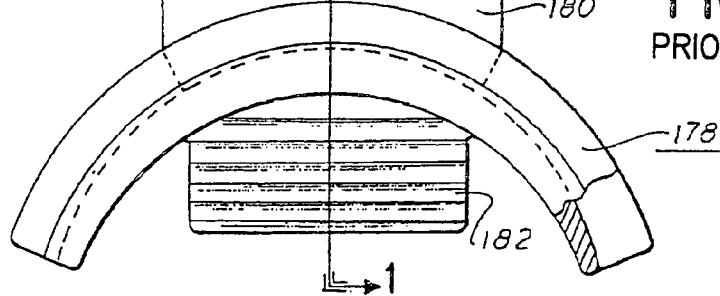

FIGS. 1-5 illustrate the prior art Buechel-Pappas Total Ankle Replacement System as described in U.S. Pat. Nos. 4,309,778 and 4,340,978. In applicants' prior art ankle replacement system, talar platform component 178 is implanted in the talus, and tibial platform component 179 is implanted in the distal tibia. Intermediate bearing component 180 is interposed between talar component 178 and tibial component 179. Talar component 178 has a superior bearing surface 181, as shown in FIG. 1, which consists of a segment of a surface of revolution produced by a generating curve, as illustrated in FIGS. 1 and 3. The generating curve may typically consist of two 0.625 inch radius circular arcs connected by two 20" tangent lines to a 0.250 inch radius circular arc.

The inferior portion of talar component 178 includes a fixation fin 182 (see FIG. 1) with serrated sides for implantation into the talus. Tibial component 179 consists of a flat plate 183 with serrated top edge 184 and a fixation fin 185, both of which are used for implantation into the tibia. The plastic intermediate bearing component 180 has an inferior bearing surface 186 complementary to the superior bearing surface 181 of talar component 178. Intermediate bearing component 180 is also provided with a flat superior bearing surface 187 which matches flat inferior bearing surface 188 of tibial component 179.

It is important to recognize that the superior bearing surface 181 of talar component 178, by virtue of its shape, acts as a track to constrain the motion of intermediate bearing component 180 relative to the talar component 178.

The ankle prosthesis illustrated in FIGS. 1-3 provides flexion-extension motion by rotation of the talar component 178 relative to the intermediate bearing component 180. There is sliding engagement of the inferior bearing surface 186 of intermediate bearing component 180 with the superior bearing surface 181 of talar component 178 as the ankle is flexed or extended, thereby providing flexion-extension motion between the tibia and the talus.

Sliding engagement of the flat superior bearing surface 187 of intermediate bearing component 180 with the flat inferior bearing surface 188 of tibial component 179 allows anterior-posterior translation as well as limited medial-lateral translation. The medial-lateral translation is constrained by anatomical features, namely, the maleali of the ankle. The anterior-posterior motion is constrained by the action of the ligaments. Thus, applicants' prior art prosthesis of FIGS. 1-3 includes no mechanical constraints against anterior-posterior or medial-lateral translation, a desirable feature because it minimizes force loads on the components of the prosthesis.

The prosthetic joint of FIGS. 1-3 also allows axial rotation, that is, rotation about the axis of the femur, without any restraint other than that provided by natural tissues. In addition, it provides unrestrained flexion-extension. The purpose of the track (i.e., the characteristic shape of the generating curve used for the superior bearing surface 181 of talar component 178) is to retain the intermediate bearing component 180 so as to prevent its moving outside the medial-lateral borders of talar component 178. In this way intermediate bearing component 180 is prevented from impinging upon adjacent bone.

Figure 4:
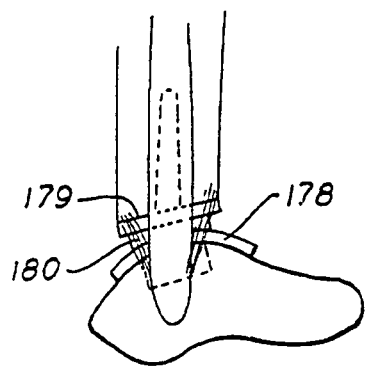
FIG. 4 is a side elevational view of an implanted prior art Buechel-Pappas Total Ankle Replacement System.
Figure 5:
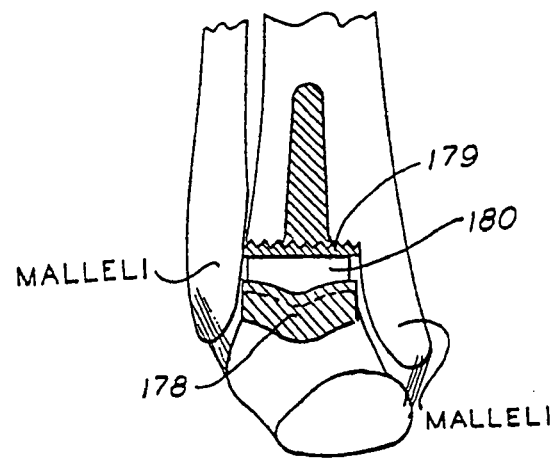
FIG. 5 is a front elevational view of an implanted prior art Buechel-Pappas Total Ankle Replacement System.
Figure 6:
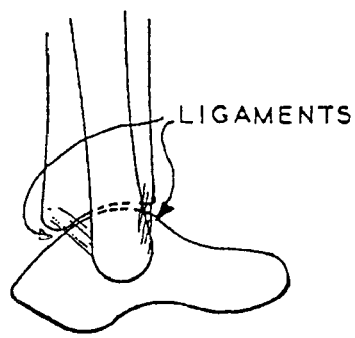
FIGS. 6 and 7 show an anatomical ankle, for comparison with the implanted prior art Buechel-Pappas Total Ankle Replacement System as shown in FIGS. 1-5.
Figure 7:
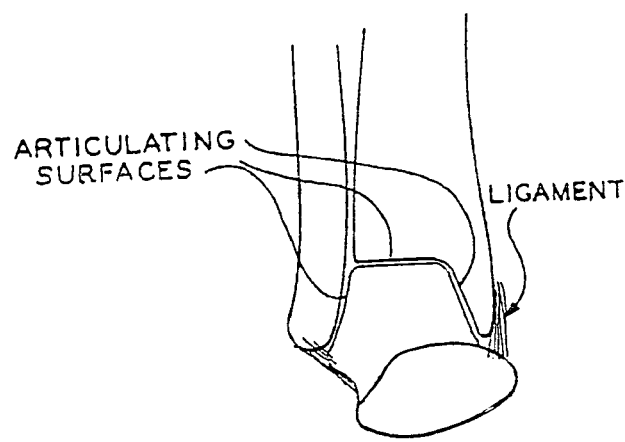

The prior art implanted prosthetic ankle is shown in FIGS. 4 and 5. Visible in FIGS. 4 and 5 are talar component 178, intermediate bearing component 180, and tibial component 179. For comparison, an anatomical ankle is illustrated in FIGS. 6 and 7.

In connection with the prior art system of FIGS. 1-5, it has been discovered that for several reasons, such as components that are too large or growth of tissue into the joint space between the tibial component and the plastic bearing, rubbing of the plastic bearing against tissue has produced wear particles that lead to the formation of bone cysts.

To reduce this possible problem, the subject invention provides a depending peripheral wall extending from the lower end of the inferior bearing platform surface of the tibial component.

Figure 8:
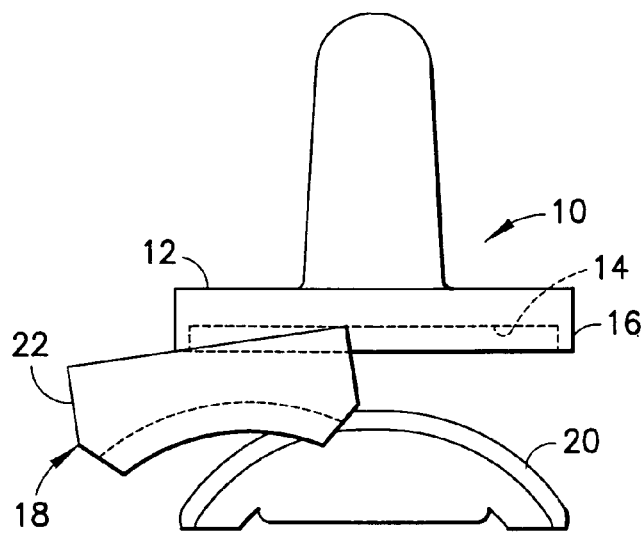
FIG. 8 is a side elevational view, partially in cross-section, of the improved ankle system of the subject invention including the tibial component with the depending wall, and wherein the bearing insert is partially inserted in the ankle prosthesis.
Figure 9:
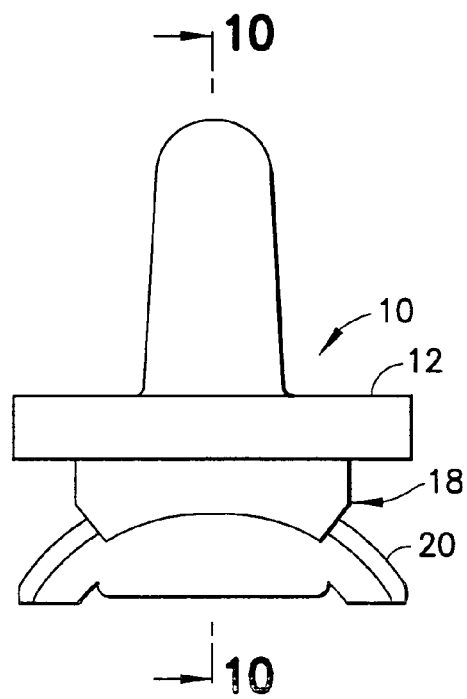
FIG. 9 is a side elevational view of the improved ankle system of the subject invention.
Figure 10:
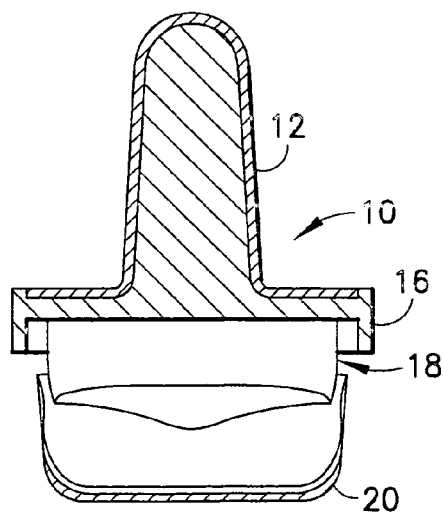
FIG. 10 is a cross-sectional view of the ankle system of the subject invention taken along line 10-10 in FIG. 9.

Turning to FIGS. 8-10, the tibial component 10 includes a flat superior bearing platform surface 12 and flat inferior bearing surface 14.

As shown in FIGS. 8-10, extending about the entire periphery of the flat inferior platform bearing surface 14 is a depending peripheral wall 16.

In FIG. 8, the plastic bearing 18 is in a position just prior to the insertion of bearing 18 between the tibial component 10 and the talar component 20.

As shown in FIG. 9, the ankle prosthesis of the subject invention is fully assembled, with the plastic bearing 18 being intermediate the tibial component 10 and the talar component 20.

In the cross-sectional view of FIG. 10, the superior bearing surface of intermediate plastic bearing 18 is in sliding contact with the flat inferior bearing surface 14 of the tibial component 10, and the depending peripheral wall 16 surrounds the perimeter edge of the plastic bearing. It is also noted that the inner peripheral edge of peripheral wall 16 is spaced from the peripheral edge of plastic bearing 18.

Figure 11A:
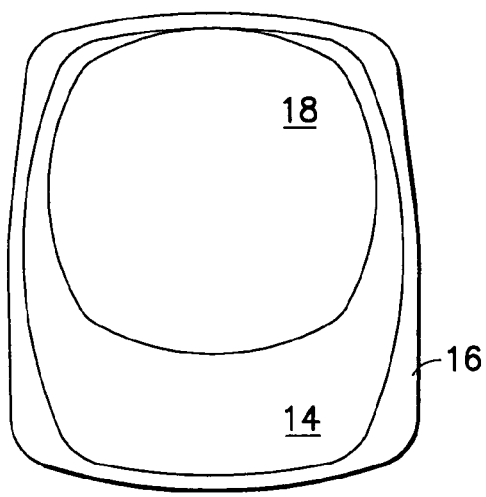
FIGS. 11A, 11B and 11C illustrate different positions of the intermediate bearing element within the tibial component with the depending wall of the subject invention.
Figure 11B:
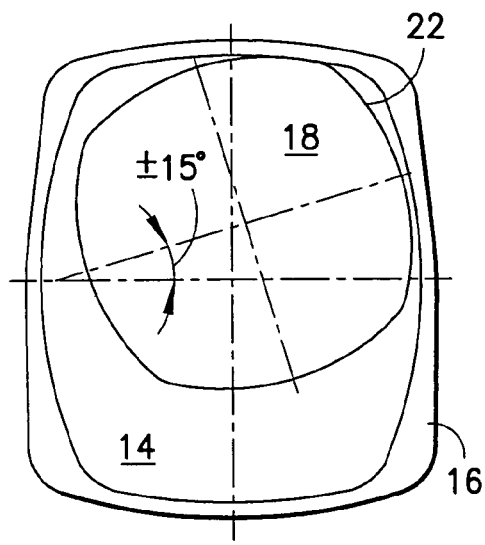
Figure 11C:
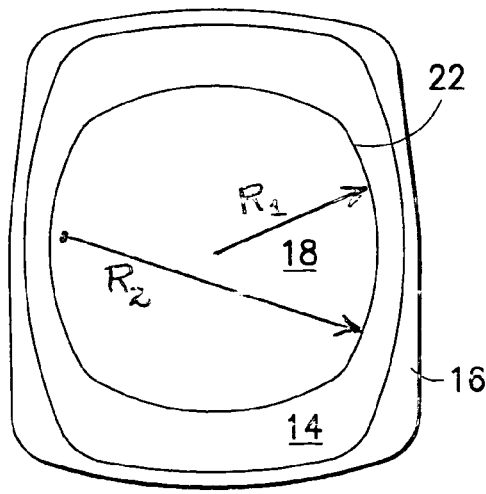

FIG. 11C shows the plastic bearing 18 in a central position within and spaced from the inner surface of the peripheral wall 16. This central position is expected to be the position of the components of the subject prosthesis during the neutral position of the foot.

As illustrated in FIG. 11C, the inside of the peripheral wall 16 and the sides 22 of the plastic bearing 18 are made curved. This is to reduce the contact stresses on the sides of the plastic bearing and therefore to reduce wear resulting from contact between the inside of the peripheral wall 16 and the sides 22 of the plastic bearing 18.

Typically, the inside radius $R_2$ of the peripheral wall 16 is about double the radius $R_1$ of the sides 22 of plastic bearing 18. This produces acceptable levels of stress in the bearing sides 22 for the contact forces expected in the ankle.

FIG. 11A shows the plastic bearing in the posterior position, and such posterior translation of the bearing is allowed in a particular size ankle replacement. Such translation may occur during use, but is unlikely.

Referring to FIG. 11B, surgical malpositioning of the tibial and talar components may produce an off center position of the bearing even in a neutral position of the foot. FIG. 11B shows such translation accompanied by rotation of the talus relative to the tibia.

Furthermore, FIG. 11B shows a rotation of 15° which is significantly beyond that normally occurring in the ankle. As shown, the contact is the same as when there is no rotation. Rotation significantly beyond that shown in FIG. 11B would produce contact with the much smaller corner radius of the plastic bearing, thereby resulting in a much higher contact stress.

Figure 12:
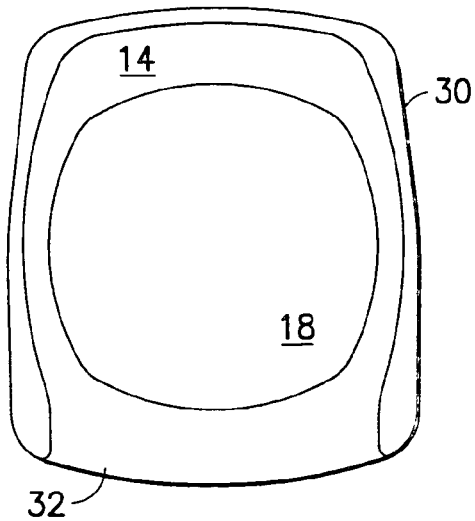
FIG. 12 is a bottom plan view of an alternate embodiment of the improved tibial component of the subject invention.

FIG. 12 illustrates another embodiment of the subject invention in which the peripheral wall 30 extends only about three sides of the inferior bearing surface 14 of the tibial component 12, with the anterior portion 32 of the tibial component being open. The anterior opening 32 in the peripheral wall 30 facilitates insertion of the plastic bearing 18 during the surgical implant procedure.

The peripheral walls 16, 30 effectively shield the plastic bearing 18 from the tissue surrounding the ankle prosthesis, thereby greatly minimizing rubbing of the bearing against tissue and thus reducing the formation of bone cysts. The peripheral walls 16 and 30 are intended to operate to reduce possible abrasion between the plastic bearing and tissue by at least partially shielding the plastic bearing within the tibial component 10.

It will be understood by those skilled in the art that many modifications and variations of the present invention may be made without departing from the spirit and the scope thereof. For example, although the preferred embodiments have described the subject invention in an ankle prosthesis, the invention may also be embodied in other types of prostheses, as, for example, those described and illustrated in applicants' prior U.S. Pat. Nos. 4,309,778 and 4,340,978.

What is claimed is:

1. An improved prosthetic joint of the type including:
   a first platform having a first bearing surface, the first platform being configured for being secured to a first bone of an anatomical joint;
   a second platform having a substantially planar second bearing surface facing towards the first platform, the second platform being configured for being secured to a second bone of the anatomical joint;
   a bearing insert having a third bearing surface slidably engaged with the first bearing surface of the first platform for sliding movement relative thereto during joint articulation, the bearing insert further having a fourth bearing surface slidably engaged with the second bearing surface of the second platform to permit rotation of the bearing insert relative to the second platform about an axis normal to the second bearing surface, the bearing insert providing an articulated joint between the first platform and the second platform;
   means for constraining motion of the bearing insert during joint articulation to a predetermined path relative to the first platform;
   wherein the improvement comprises:
   a peripheral wall extending from said second bearing surface and about said bearing insert to shield the bearing insert from contacting anatomical tissue for reducing the formation of bone cysts, the peripheral wall defining an inner periphery that is dimensioned relative to the bearing insert for permitting translation between the bearing insert and the second bearing surface defined on the second platform in directions parallel to the second bearing surface, and wherein all of the bearing insert is within a projection of the peripheral wall from the second bearing surface towards the first platform and wherein all cross sections through the bearing insert and parallel to the second bearing surface are smaller than the second bearing surface.

2. An improved prosthetic joint as recited in claim 1, wherein the means for constraining motion of the bearing insert during joint articulation to a predetermined path relative to the first platform comprises: a track surface provided on one of the first platform or the bearing insert and a track surface follower provided on the other of said first platform or the bearing insert, the track surface follower slidably engaging the track surface.

3. An improved prosthetic joint as recited in claim 2, wherein the track surface comprises a curved track surface.

4. An improved prosthetic joint as recited in claim 1, wherein said peripheral wall extends about the entire periphery of said second platform.

5. An improved prosthetic joint as recited in claim 1 wherein said peripheral wall extends about the periphery of said second bearing surface, except in the anterior portion of said prosthetic joint to facilitate the insertion of the bearing insert during a surgical implant procedure.

6. An improved prosthetic joint as recited in claim 1, wherein the bearing insert is a plastic bearing, sides of the plastic bearing are curved, and the inner surface of the peripheral wall is also curved, with the curvature of the plastic bearing and the peripheral wall being configured to reduce contact stresses therebetween in the event that touching of these surfaces does occur during flexure of the ankle prosthesis.

7. An improved prosthetic joint of the type including;
   a first platform having a first bearing surface, the first platform being configured for being secured to a first bone of an anatomical joint;
   a second platform having a substantially planar second bearing surface facing towards the first platform, the second platform being configured for being secured to a second bone of the anatomical joint;
   a plastic bearing having a third bearing surface which slidably engaged with the first bearing surface of the first platform for sliding movement relative thereto during joint articulation, the plastic bearing further having a fourth bearing surface slidably engaged with the second bearing surface of the second platform to permit rotation of the bearing insert relative to the second platform about an axis normal to the second bearing surface, the plastic bearing providing an articulated joint between the first platform means and the second platform means;
   means for constraining motion of the plastic bearing during joint articulation to a predetermined path relative to the first platform;
   wherein the improvement comprises:
   said second platform including a peripheral wall extending from said second bearing surface and about said bearing insert to shield the plastic bearing from contacting anatomical tissue for reducing the formation of bone cysts, the peripheral wall defining an inner surface that is dimensioned relative to the plastic bearing for permitting translation between the plastic bearing and the second bearing surface defined on the second platform in directions parallel to the second bearing surface, sides of the plastic bearing being curved and the inner surface of the peripheral wall also being curved, with the curvature of the plastic bearing and the peripheral wall being configured to reduce contact stresses therebetween in the event that touching of these surfaces does occur during flexure of the ankle prosthesis, wherein the radius of the inner surface of the peripheral wall is about twice the radius of the curvature of the plastic bearing.

8. An improved prosthetic ankle joint of the type including:
   a talar component including a first bearing surface, the talar component being adapted to be secured to the talus of an anatomical ankle joint;
   a bearing insert having a second bearing surface that slidably engages the first bearing surface of the talar component for sliding movement relative thereto during ankle articulation, the bearing insert having a substantially planar third bearing surface, the bearing insert providing an articulated joint between the talar component and the talus of said ankle joint;
   a tibial component having a substantially planar fourth bearing surface which slidably engages the third bearing surface of the bearing insert for permitting rotation of the bearing insert relative to the tibial component about an axis normal to the fourth bearing surface, the tibial component being adapted to be secured to the tibia of an anatomical ankle joint;
   means for constraining motion of the bearing insert during ankle joint articulation to a predetermined path relative to the talar component wherein the improvement comprises:
   said tibial component including a peripheral wall extending from said fourth bearing surface and about said bearing insert to shield the bearing insert from contacting anatomical tissue for reducing the formation of bone cysts, the peripheral wall defining an inner periphery dimensioned relative to the bearing insert for permitting substantially planar translation between the bearing insert and the tibial component in directions parallel to the substantially planar fourth bearing surface and wherein no part of the bearing insert projects out beyond an inner periphery of the peripheral wall in directions parallel to the fourth bearing surface.

9. An improved prosthetic ankle joint as recited in claim 8 wherein the means for constraining motion of the bearing insert during joint articulation to a predetermined path relative to the talar component comprises:
   a track surface provided on one of the talar component or the bearing insert and a track surface follower provided on the other of said talar component or the bearing insert, the track surface follower slidably engaging the track surface.

10. An improved prosthetic ankle joint as recited in claim 9 wherein the track surface comprises curved track surface.

11. An improved prosthetic ankle joint as recited in claim 8 wherein said peripheral wall extends about the entire periphery of said tibial component.

12. An improved prosthetic ankle joint as recited in claim 8 wherein said peripheral wall extends about the periphery of said fourth bearing surface, except in the anterior portion of said ankle joint to facilitate the insertion of the bearing insert during a surgical implant procedure.

13. An improved prosthetic ankle joint as recited in claim 8 further comprising retention means, the retention means for preventing dislocation of the bearing insert from the talar component during the normal range of ankle joint motion.

14. An improved prosthetic ankle joint comprising:
   a talar component including a first bearing surface, the talar component being adapted to be secured to the talus of an anatomical ankle joint;
   a bearing insert having a second bearing surface that slidably engages the first bearing surface of the talar component for sliding movement relative thereto during ankle articulation, the bearing insert having a substantially planar third bearing surface, the bearing insert providing an articulated joint between the talar component and the talus of said ankle joint;
   a tibial component having a substantially planar fourth bearing surface which slidably engages the third bearing surface of the bearing insert for permitting rotation of the bearing insert relative to the tibial component about an axis normal to the fourth bearing surface, the tibial component being adapted to be secured to the tibia of an anatomical ankle joint;
   means for constraining motion of the bearing insert during ankle joint articulation to a predetermined path relative to the talar component wherein the improvement comprises:
   said tibial component including a peripheral wall extending from said fourth bearing surface and about said bearing insert to shield the bearing insert from contacting anatomical tissue for reducing the formation of bone cysts, the peripheral wall defining an inner periphery dimensioned relative to the bearing insert for permitting translation between the bearing insert and the tibial component in directions parallel to the fourth bearing surface, wherein no part of the bearing insert projects out beyond an inner periphery of the peripheral wall in directions parallel to the fourth bearing surface wherein the sides of the bearing insert are curved, and the inner surface of the peripheral wall is also curved, with the curvature of the bearing insert and the peripheral wall being configured to reduce contact stresses therebetween in the event that touching of these surfaces does occur during flexure of the ankle prosthesis.

15. An improved prosthetic ankle joint as recited in claim 14 wherein the radius of curvature of the inner surface of the peripheral wall is about double the radius of curvature of the sides of the bearing insert.

16. An improved prosthetic ankle joint of the type including:
   a talar component including a first bearing surface, the talar component being adapted to be secured to the talus of an anatomical ankle joint;
   a bearing insert having a second bearing surface that slidably engages the first bearing surface of the talar component for sliding movement relative thereto during ankle articulation, the bearing insert having a third bearing surface, the bearing insert providing an articulated joint between the talar component and the talus of said ankle joint;
   a tibial component having a substantially planar fourth bearing surface which slidably engages the third bearing surface of the bearing insert for permitting rotation of the bearing insert relative to the tibial component about an axis normal to the fourth bearing surface, the tibial component being adapted to be secured to the tibia of an anatomical ankle joint;
   means for constraining motion of the bearing insert during ankle joint articulation to a predetermined path relative to the talar component wherein the improvement comprises:
   said tibial component including a peripheral wall extending from said fourth bearing surface and about said bearing insert to shield the bearing insert from contacting anatomical tissue for reducing the formation of bone cysts, the peripheral wall defining an inner periphery dimensioned relative to the bearing insert for permitting translation between the bearing insert and the tibial component in directions parallel to the fourth bearing surface wherein all cross sections through the bearing insert and parallel to the fourth bearing surface are smaller than the fourth bearing surface; and
   retention means for preventing dislocation of the bearing insert from the talar component during the normal range of angle joint motion, wherein the retention means comprises:
   (a) portions of one of the bearing insert or the talar component defining a dovetail projection; and,
   (b) portions of the other of the bearing insert or the talar component defining track means having a complimentary dovetail cross-section within which the dovetail projection is slidably retained.

17. An improved prosthetic ankle joint of the type including:
   a talar component including a first bearing surface, the talar component being adapted to be secured to the talus of an anatomical ankle joint;
   a bearing insert having a second bearing surface that slidably engages the first bearing surface of the talar component for sliding movement relative thereto during ankle articulation, the bearing insert having a substantially planar third bearing surface, the bearing insert providing an articulated joint between the talar component and the talus of said ankle joint;
   a tibial component having a substantially planar fourth bearing surface which slidably engages the third bearing surface of the bearing insert for permitting rotation of the bearing insert relative to the tibial component about an axis normal to the fourth bearing surface, the tibial component being adapted to be secured to the tibia of an anatomical ankle joint;

means for constraining motion of the bearing insert during ankle joint articulation to a predetermined path relative to the talar component wherein the improvement comprises:

said tibial component including a peripheral wall extending from said fourth bearing surface and about said bearing insert to shield the bearing insert from contacting anatomical tissue for reducing the formation of bone cysts, the peripheral wall defining an inner periphery dimensioned relative to the bearing insert for permitting substantially planar translation between the bearing insert and the tibial component in directions parallel to the substantially planar fourth bearing surface, wherein all cross sections through the bearing insert and parallel to the fourth bearing surface are smaller than the fourth bearing surface.

* * * * *